(12) United States Patent
Yamauchi et al.

(10) Patent No.: US 9,713,800 B2
(45) Date of Patent: Jul. 25, 2017

(54) MULTI-TUBULAR REACTOR AND MULTI-TUBULAR REACTOR DESIGN AND FABRICATION METHOD

(71) Applicant: SUMITOMO CHEMICAL COMPANY, LIMITED, Chuo-ku, Tokyo (JP)

(72) Inventors: Shingo Yamauchi, Niihama (JP); Tamotsu Takamoto, Niihama (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 0 days.

(21) Appl. No.: 14/389,948

(22) PCT Filed: Apr. 3, 2013

(86) PCT No.: PCT/JP2013/060253
§ 371 (c)(1),
(2) Date: Oct. 1, 2014

(87) PCT Pub. No.: WO2013/151108
PCT Pub. Date: Oct. 10, 2013

(65) Prior Publication Data
US 2015/0328611 A1    Nov. 19, 2015

(30) Foreign Application Priority Data

Apr. 4, 2012  (JP) .................................. 2012-085158

(51) Int. Cl.
*B01J 8/06* (2006.01)
*B01J 8/00* (2006.01)
(Continued)

(52) U.S. Cl.
CPC ............... *B01J 8/067* (2013.01); *B01J 8/001* (2013.01); *C07C 45/34* (2013.01); *C07C 45/35* (2013.01);
(Continued)

(58) Field of Classification Search
CPC . B01J 8/06; C07C 45/37; C07C 45/34; C07C 51/21; C07C 51/25
(Continued)

(56) References Cited

U.S. PATENT DOCUMENTS 4,440,509 A    4/1984  Agarwal
6,582,667 B1   6/2003  Ogata et al.
(Continued)

FOREIGN PATENT DOCUMENTS

CN    1697811 A       11/2005
DE    10127374 A1     12/2002
(Continued)

OTHER PUBLICATIONS

Heat Exchanger Designing Handbook (revised edition), May 25, 1986 (S61), pp. 402-407 with Partial English Translation.
(Continued)

*Primary Examiner* — Walter D Griffin
*Assistant Examiner* — Huy-Tram Nguyen
(74) *Attorney, Agent, or Firm* — Sughrue Mion, PLLC

(57) ABSTRACT

A multi-tubular reactor (1) comprising a cylindrical shell (2), a plurality of reaction tubes (10) located in the shell, and a disk-and-doughnut type baffle (5), wherein
the reaction tubes (10) are arranged so as to be in a triangular configuration,
one or more of the reaction tubes (10) is/are a temperature-measuring reaction tube(s) provided with a thermometer (20), and
a line (BL) through a central axis of the temperature-measuring reaction tube and a central axis of the shell
(Continued)

(2) forms an angle from 0 to 15 degree with a line (CL) through the central axis of the temperature-measuring reaction tube and a central axis of at least one adjacent reaction tube next to the temperature-measuring reaction tube, in a cross section of the reactor (1) perpendicular to the central axis of the shell (2), as well as a design and production method thereof.

22 Claims, 7 Drawing Sheets

(51) Int. Cl.
    C07C 45/37    (2006.01)
    C07C 45/34    (2006.01)
    C07C 51/21    (2006.01)
    C07C 45/35    (2006.01)
    C07C 51/25    (2006.01)
(52) U.S. Cl.
    CPC .............. *C07C 45/37* (2013.01); *C07C 51/21* (2013.01); *C07C 51/252* (2013.01); *B01J 2208/0023* (2013.01); *B01J 2208/00044* (2013.01); *B01J 2208/00212* (2013.01); *B01J 2208/00221* (2013.01); *B01J 2208/065* (2013.01); *Y10T 29/49828* (2015.01)
(58) Field of Classification Search
    USPC ........................................................ 422/652
    See application file for complete search history.

(56) References Cited

U.S. PATENT DOCUMENTS

| | | | |
|---|---|---|---|
| 6,613,940 | B1 | 9/2003 | Nishimura et al. |
| 6,808,689 | B1 | 10/2004 | Matsumoto et al. |
| 7,119,227 | B2 | 10/2006 | Sakakura et al. |
| 7,297,814 | B2 | 11/2007 | Yada et al. |
| 7,667,072 | B2 | 2/2010 | Yada et al. |
| 7,771,674 | B2 | 8/2010 | Suzuta et al. |
| 7,988,927 | B2 | 8/2011 | Lehr et al. |
| 2004/0126285 | A1 | 7/2004 | Olbert et al. |
| 2005/0118088 | A1* | 6/2005 | Olbert ............... B01J 8/001 423/416 |
| 2005/0131254 | A1 | 6/2005 | Yada et al. |
| 2007/0049769 | A1 | 3/2007 | Sugiyama et al. |
| 2008/0021238 | A1 | 1/2008 | Yamagishi et al. |
| 2008/0300414 | A1 | 12/2008 | Schliephake et al. |

FOREIGN PATENT DOCUMENTS

| | | | |
|---|---|---|---|
| EP | 1 080 780 A1 | 3/2001 | |
| EP | 1 080 781 A1 | 3/2001 | |
| JP | S58-180920 A | 10/1983 | |
| JP | 2000-93784 A | 4/2000 | |
| JP | 2001-137688 A | 5/2001 | |
| JP | 2001-139499 A | 5/2001 | |
| JP | 2003-206244 A | 7/2003 | |
| JP | 2003-321404 A | 11/2003 | |
| JP | 2003-340267 A | 12/2003 | |
| JP | 2004-26799 A | 1/2004 | |
| JP | 2004000944 A | 1/2004 | |
| JP | 2005-296921 A | 10/2005 | |
| JP | 2005-336142 A | 12/2005 | |
| JP | 2006-510471 A | 3/2006 | |
| JP | 2006-142299 A | 6/2006 | |
| JP | 2006-150357 A | 6/2006 | |
| JP | 2007-326053 A | 12/2007 | |
| JP | 2008-30033 A | 2/2008 | |
| JP | 2008-100195 A | 5/2008 | |
| JP | 2010529005 A | 8/2010 | |
| JP | 2012-16670 A | 1/2012 | |
| WO | 2004/052524 A1 | 6/2004 | |
| WO | 2005/005037 A1 | 1/2005 | |

OTHER PUBLICATIONS

English translation of International Search Report mailed Jul. 9, 2013 in International Application No. PCT/JP2013/060253.
English translation of International Preliminary Report on Patentability issued Oct. 7, 2014 in International Application No. PCT/JP2013/060253.
Communication dated Aug. 7, 2015, issued by the State Intellectual Property Office of the People's Republic of China in corresponding Chinese Application No. 201380018435.2.
Communication dated Jul. 30, 2015, informing that the anonymous third-party observation was filed on Jul. 14, 2015, issued by the European Patent Office in corresponding European Application No. 13772258.3.
Notification dated Jun. 16, 2015, issued by the Japan Patent Office informing that the third-party observation by Submission of information was filed on May 18, 2015, in corresponding Japanese Application No. 2012-085158.
Third Party Submission dated Feb. 5, 2016, issued by the Japanese Patent Office in corresponding Japanese Application No. 2012-085158.
Communication dated Mar. 8, 2016, issued by the Japan Patent Office in corresponding Japanese Application No. 2012-085158.
Communication dated Apr. 5, 2016 from the Japanese Patent Office in counterpart application No. 2012-085158.
English translation of communication dated Nov. 10, 2015 from the Japanese Patent Office issued in counterpart Japanese application No. 2012-085158.
Communication dated Nov. 9, 2015, from the European Patent Office in counterpart European Application No. 13772258.3.
Communication dated Jun. 24, 2016 from the State Intellectual Property Office of the P.R.C. issued in corresponding Application No. 201380018435.2.
Communication dated Mar. 13, 2017, from the European Patent Office in counterpart European application No. 13772258.3.
Communication dated Mar. 20, 2017, from the State Intellectual Property Office of the P.R.C., in counterpart Chinese application No. 201380018435.2.
Communication dated Feb. 21, 2017, issued from the Japan Patent Office in corresponding Japanese Patent Application No. 2012-085158.

\* cited by examiner

Flow Condition at 0 degree (A)

Flow Condition at 10 degree (B)

(A)

(B)

Change of tube-outside film heat transfer coefficient (unit: W/(m²·K))

| Angle | Flow of Heat Transfer Medium/ Reaction Tube Number (m³/number) | | | Improvement Rate (%) | | |
|---|---|---|---|---|---|---|
| | 0.2 | 0.3 | 0.4 | 0.2 | 0.3 | 0.4 |
| 0 | 1670.1 | 1849.2 | 2123.9 | 100.0 | 100.0 | 100.0 |
| 5 | 1665 | 1840.4 | 2123.2 | 99.7 | 99.5 | 100.0 |
| 10 | 1667.8 | 1853.6 | 2155.3 | 99.9 | 100.2 | 101.5 |
| 15 | 1690.5 | 1888.5 | 2194.8 | 101.2 | 102.1 | 103.3 |
| 20 | 1716.2 | 1915.6 | 2237.6 | 102.8 | 103.6 | 105.4 |
| 25 | 1734.7 | 1960.1 | 2280.8 | 103.9 | 106.0 | 107.4 |
| 30 | 1743.1 | 1970.2 | 2282 | 104.4 | 106.5 | 107.4 |

(A)

(B)

MULTI-TUBULAR REACTOR AND MULTI-TUBULAR REACTOR DESIGN AND FABRICATION METHOD

CROSS REFERENCE TO RELATED APPLICATIONS

This application is a National Stage of International Application No. PCT/JP2013/060253 filed Apr. 3, 2013, claiming priority based on Japanese Patent Application No. 2012-085158, filed Apr. 4, 2012, the contents of all of which are incorporated herein by reference in their entirety.

TECHNICAL FIELD

The present invention relates to a multi-tubular reactor as well as a design of a multi-tubular reactor and a production method thereof. More specifically, the present invention relates to a multi-tubular reactor comprising a cylindrical shell, a plurality of reaction tubes provided in the shell, and a disk-and-doughnut type baffle, as well as a design of such multi-tubular reactor and a production method thereof.

BACKGROUND ART

An intended substance (hereinafter, which may be referred to as an "object substance" or an "object product") can be produced in a multi-tubular reactor (or a so-called shell-and-tube type reactor) wherein a plurality of straight reaction tubes (having diameter of about few centimeters (cm)) are accommodated in a cylindrical shell so that the reaction tubes are located in parallel with the central axis of the shell. Herein, for example, a catalyst has been filled in the reaction tube, a raw material gas is supplied into the reaction tube, and the raw material gas is subjected to a reaction while the raw material gas flows in the reaction tube in one direction.

In the reaction of the raw material gas in such reaction tube, its reaction temperature is very important in order to efficiently provide the object substance. Therefore, in the multi-tubular reactor, the temperature of the reaction tube can be controlled so as to be in an appropriate reaction temperature. Herein, for example, a fused salt such as sodium nitrite and potassium nitrate (HTS: Heat Transfer Salt) is used as a heat transfer medium. The heat transfer medium is supplied and filled inside the shell (specifically, between the shell and the reaction tubes provided therein). The heat transfer medium flows in the shell. For example, in the exothermic reaction, the reaction-heat generated from the reaction is removed by the heat transfer medium. In the endothermic reaction, the heat required for the reaction is supplied from the heat transfer medium to the reaction tube in order to heat the raw material gas therein. Accordingly, the temperature of the reaction tube is controlled so as to be in an appropriate reaction temperature.

In order to efficiently carry out the removal or addition of the heat by the heat transfer medium, it is required that the heat transfer medium efficiently comes into contact with many reaction tubes. Therefore, conventionally, in order to improve the contacting efficiency between the heat transfer medium and the reaction tube, arrangement of the reaction tubes is adjusted, or a baffle board(s) (or a baffle(s)) is/are provided in the shell of the multi-tubular reactor in order to control the flow of the heat transfer medium. By the improvement of the contacting efficiency between the heat transfer medium and the reaction tube, the efficiency of the removal or addition of the heat from/to the reaction tube by the heat transfer medium can be improved (see non-patent literature 1).

However, the number of the reaction tubes to be located in the multi-tubular reactor is few thousands or tens of thousands when they are many. Herein, a number of the reaction tubes can be arranged each other in a distance of about few millimeters (mm). Therefore, even if the arrangement of the reaction tubes is adjusted, or a baffle board(s) is/are provided in the shell of the multi-tubular reactor, it is extremely difficult for all the reaction tubes to be improved regarding the contact-circumstance between the heat transfer medium and the reaction tubes. Therefore, there could be a reaction tube on which the removal or addition of the heat by the heat transfer medium cannot be efficiently carried out. Herein, in case of that there is a reaction tube having such deteriorated heat-removing efficiency, an extremely elevated temperature part (or a hot spot) may be formed on the reaction tube due to accumulation of the reaction-heat, etc. Alternatively, an extremely lowered temperature part (or a cold spot) may be formed due to insufficient heating. In case of such hot spot or cold spot is formed, it is not easy to appropriately carry out the reaction of the raw material gas, and therefore, problems may be arisen wherein production efficiency of the object substance is lowered. Accordingly, the multi-tubular reactor is necessarily controlled in order to prevent the formation of such hot spot or cold spot.

As an art preventing the formation of the hot spot or cold spot, for example, those detecting location(s) where the hotspot part may be formed by measuring temperature of the catalyst in the reaction tube, and the like, are disclosed (in patent literature 1).

Patent literature 1 discloses arts for measuring the temperature of the catalyst by providing reaction tube groups formed by a plurality of reaction tubes in a fixed bed multi-tubular reactor, and providing catalyst temperature measures to all of the reaction tube groups or a part of the reaction tubes thereof. Herein, it is disclosed that presence or absence of the hotspot part is monitored by the catalyst temperature measures attached to the reaction tube groups, and that a gas phase catalytic oxidation reaction can be operated stably with high efficiency by controlling the reaction based on the measured results (see patent literature 1: page 5, lines 43-46 of the description).

Furthermore, patent literature 1 poses problems, when the number of the reaction tubes is large, difference of the flow pattern of the heat transfer medium in the fixed-bed multi-tubular reactor tends to become larger so that the difference of the flow pattern causes a change in the heat transfer state on the reaction tube. Herein, it is also disclosed that the reaction tube groups provided with the catalyst temperature measures are allocated to the portions where the flow patterns of the heat transfer medium flowing outside the reaction tubes are different, and it is possible to understand the temperature in the fixed-bed multi-tubular reactor more precisely (patent literature 1, page 5, lines 23-38 in the description).

Herein, as it is described above, patent literature 1 discloses that the allocation of the reaction tube groups provided with the catalyst temperature measures to the portions where the flow patterns of the heat transfer medium are different, and therefore it is possible to understand the temperature in the fixed-bed multi-tubular reactor more precisely. However, there is no specific description with respect to any relation between the flow pattern and the location where the hotspot part can be formed.

Patent literature 1 discloses and explains on the assumption that the fixed bed multi-tubular reactor employs a partially cut circular baffle board(s) (e.g., D-cut baffle board(s), semicircular baffle board(s), etc.) as a baffle board. It is considered in view of the flow pattern of FIG. 5 of the patent literature 1 (see non-patent literature 1, page 405).

However, the partially-cut circular baffle board can be applied to only a small type multi-tubular reactor (having reaction tubes which number is less than 10000). When the partially-cut circular baffle board is applied to a large type multi-tubular reactor (having reaction tubes which number is no less than 10000), flow resistance of the heat transfer medium flowing in the shell would be increased. Therefore, it is a rare case where the partially-cut circular baffle board(s) is/are employed in a large type multi-tubular reactor. Whereas, there are many cases where a circular baffle board(s) (i.e., a disk-and-doughnut type baffle board(s)) is/are employed. In order to appropriately control the reaction in such large type multi-tubular reactor, it is difficult to presume how to measure the temperature of the reaction tube and where such measurement is to be carried out in view of the arts which are disclosed in the patent literature 1.

PRIOR ART LITERATURES

Patent Literatures

Patent Literature 1: WO 2005/005037

Non-Patent Literature

Non-patent Literature 1: "Heat Exchanger Designing Handbook (revised edition)" written by Hideaki Ohana, Kougakutosho Ltd., May 25, 1986 (S61), pp 402-407.

SUMMARY OF INVENTION

Problems to be Solved by Invention

Regarding the above-described circumstances, objects of the present invention consist in a provision of a multi-tubular reactor which can appropriately control a reaction so that formation of a hot spot or a cold spot is prevented during any production of a substance with an exothermic or endothermic reaction, as well as a provision of a design of such multi-tubular reactor and a production method thereof.

Means for Solving Problems (Multi-Tubular Reactor)
[1]
A multi-tubular reactor comprising a cylindrical shell, a plurality of reaction tubes located in the shell, and a disk-and-doughnut type baffle, characterized in that
the reaction tubes are arranged so as to be in a triangular configuration,
one or more of the reaction tubes is/are a temperature-measuring reaction tube(s) provided with a thermometer, and
a line through a central axis of the temperature-measuring reaction tube and a central axis of the shell (hereinafter, which line may be referred to as a "base line") forms an angle from 0 to 15 degree with a line through the central axis of the temperature-measuring reaction tube and a central axis of at least one adjacent reaction tube next to the temperature-measuring reaction tube (hereinafter, which line may be referred to as a "connect line"), in a cross section of the reactor perpendicular to the central axis of the shell.

(Hereinafter, it may be referred to as a "first invention".)
[2]
The multi-tubular reactor according to the item [1], characterized in that the reactor is a fixed bed multi-tubular reactor to be used for a gas-solid heterogeneous reaction.

(Hereinafter, it may be referred to as a "second invention".)
[3]
The multi-tubular reactor according to the item [2], characterized in that propylene, isobutylene, t-butyl alcohol, or a mixture of two or more thereof is oxidized in a gas phase with a gas containing molecular oxygen to produce (meth) acrolein and/or (meth)acrylic acid.

(Hereinafter, it may be referred to as a "third invention".)
[4]
The multi-tubular reactor according to any one of the items [1] to [3], characterized in that the shell has an inner diameter of 3 m or more.

(Hereinafter, it may be referred to as a "forth invention".)
[5]
The multi-tubular reactor according to any one of the items [1] to [4], characterized in that the number of the reaction tubes located in the shell is 5000 or more.

(Hereinafter, it may be referred to as a "fifth invention".)
[6]
The multi-tubular reactor according to any one of the items [1] to [5], characterized in that a ratio (L/D) of a length (L) between central axes of two reaction tubes next to each other relative to an outer diameter (D) of the reaction tubes is from 1.2 to 1.6.

(Hereinafter, it may be referred to as a "sixth invention".)
[7]
The multi-tubular reactor according to any one of the items [1] to [6], characterized in that a heat transfer medium flows in the cylindrical shell and comes into contact with the reaction tubes.

(Hereinafter, it may be referred to as a "seventh invention".)
[8]
The multi-tubular reactor according to any one of the items [1] to [7], characterized in that a part where the heat transfer medium contacts with the reaction tube has a length of 1.3 m or more.

(Hereinafter, it may be referred to as an "eighth invention".)
[9]
The multi-tubular reactor according to any one of the items [1] to [8], characterized in that the temperature-measuring reaction tube is located in a sector area having a central angle of 30° in a cross section of the reactor perpendicular to the central axis of the cylindrical shell.

(Hereinafter, it may be referred to as a "ninth invention".)
(Design of Multi-Tubular Reactor and Production Method Thereof)
[10]
A design or production method of a multi-tubular reactor comprising a cylindrical shell, a plurality of reaction tubes located in the shell, and a disk-and-doughnut type baffle, characterized in that the method comprises:
arranging the reaction tubes so as to be in a triangular configuration, and
providing a thermometer to one or more of the reaction tube(s) to form a temperature-measuring reaction tube(s), wherein a line (or base line) through a central axis of the temperature-measuring reaction tube and a central axis of the shell forms an angle from 0 to 15 degree with a line (or connect line) through the central axis of the temperature-measuring reaction tube and a central axis of at least one adjacent reaction tube next to the temperature-measuring reaction tube, in a cross section of the reactor perpendicular to the central axis of the shell.

(Hereinafter, it may be referred to as a "tenth invention".)

[11]

The design or production method according to the item [10], characterized in that the multi-tubular reactor is a fixed bed multi-tubular reactor to be used for a gas-solid heterogeneous reaction.

(Hereinafter, it may be referred to as an "eleventh invention".)

[12]

The design or production method according to the item [11], characterized in that propylene, isobutylene, t-butyl alcohol, or a mixture of two or more thereof is oxidized in a gas phase with a gas containing molecular oxygen to produce (meth)acrolein and/or (meth)acrylic acid during the gas-solid heterogeneous reaction.

(Hereinafter, it may be referred to as a "twelfth invention".)

[13]

The design or production method according to any one of the items [10] to [12], characterized in that the shell has an inner diameter of 3 m or more.

(Hereinafter, it may be referred to as a "thirteenth invention".)

[14]

The design or production method according to any one of the items [10] to [13], characterized in that the number of the reaction tubes located in the shell is 5000 or more.

(Hereinafter, it may be referred to as a "fourteenth invention".)

[15]

The design or production method according to any one of the items [10] to [14], characterized in that the reaction tubes are located in the shell so that a ratio (L/D) of a length (L) between central axes of two reaction tubes next to each other relative to an outer diameter (D) of the reaction tubes is from 1.2 to 1.6.

(Hereinafter, it may be referred to as a "fifteenth invention".)

[16]

The design or production method according to any one of the items [10] to [15], characterized in that a heat transfer medium flows in the cylindrical shell and comes into contact with the reaction tubes.

(Hereinafter, it may be referred to as a "sixteenth invention".)

[17]

The design or production method according to any one of the items [10] to [16], characterized in that a part where the heat transfer medium contacts with the reaction tube has a length of 1.3 m or more.

(Hereinafter, it may be referred to as a "seventeenth invention".)

[18]

The design or production method according to any one of the items [10] to [17], characterized in that the temperature-measuring reaction tube is located in a sector area having a central angle of 30° in a cross section of the reactor perpendicular to the central axis of the cylindrical shell.

(Hereinafter, it may be referred to as an "eighteenth invention".)

Effect of Invention (Multi-Tubular Reactor)

According to the first invention, the multi-tubular reactor according to the present invention is provided with a disk-and-doughnut type baffle(s). Therefore, when a heat transfer medium is supplied into a shell, in the shell, a flow of a heat transfer medium directing to the periphery of the shell from the central axis of the shell or a flow of the heat transfer medium directing to the central axis of the shell from the periphery of the shell can be formed. However, in case of an angle between the base line and the connect line is within a range from 0 to 15 degree, these reaction tubes are in situation their contacting efficiencies with the heat transfer medium are deteriorated. Therefore, on these reaction tubes, there is increased possibility of formation of a part where the heat transfer is deteriorated between these reaction tubes and the heat transfer medium. Herein, according to the present invention, a thermometer is provided to such reaction tube to form a temperature-measuring reaction tube. Data of the temperature measured by the temperature-measuring reaction tube is utilized. Therefore, the condition in the shell can be appropriately controlled so as to prevent any formation of hot spot or cold spot.

According to the second invention, even in case of the substance is produced by a gas-solid heterogeneous reaction, the condition in the shell can be appropriately controlled not to form any hot spot or cold spot.

According to the third invention, although the reaction generating (meth)acrolein and/or (meth) acrylic acid is an exothermic reaction, the condition in the shell can be appropriately controlled not to form any hot spot.

According to the forth invention, even in case of the diameter of the shell is large, the reaction proceeding in the reaction tube can be exactly monitored so that the condition in the shell can be appropriately controlled.

According to the fifth invention, even in case of a lot of reaction tubes are provided, the condition in the shell can be appropriately understood by a small number of the thermometers. Herein, the number of the thermometers provided to the reaction tubes can be reduced. Therefore, setting up the reactor for its operation can be carried out in a short time in case of the number of the reaction tubes is large. Herein, structure of the multi-tubular reactor is not to be complicated in comparison with the case a large number of the thermometers are provided.

According to the sixth invention, when the heat transfer medium is supplied into the shell, flow resistance of the heat transfer medium can be decreased, and the contacting condition between the heat transfer medium and the reaction tubes can be improved.

According to the seventh invention, the heat transfer medium can flow in the shell, the heat transfer medium can contact with the reaction tube, and the flowing condition of the heat transfer medium, and the contacting efficiency with the reaction tube, and heat transfer can be improved.

According to the eighth invention, the reaction occurring in the reaction tube can be appropriately controlled so that the temperature difference between any locations in the axial direction of the reaction tube can be decreased even in case of the reaction tube is longer.

According to the ninth invention, the flow of the heat transfer medium is symmetry about an axis, the same flowing condition pattern can be repeated about the central axis of the shell every 30 degree. Therefore, by allocating the temperature-measuring reaction tube(s) to an area every 30 degree in a cross section of the shell, the entire reaction condition in the reactor can be understood. Therefore, the condition in the shell can be appropriately determined. Thus, according to the ninth invention, the number of the temperature-measuring reaction tubes can be further reduced.

(Design and Production Method of Multi-Tubular Reactor)

According to the tenth invention, the multi-tubular reactor according to the present invention is provided with a disk-and-doughnut type baffle(s). Therefore, when a heat transfer medium is supplied into a shell, in the shell, a flow of the heat transfer medium directing to the periphery of the shell from the central axis of the shell or a flow of the heat transfer medium directing to the central axis of the shell from the periphery of the shell can be formed. However, in case of an angle between the base line and the connect line is within a range from 0 to 15 degree, these reaction tubes are in situation their contacting efficiencies with the heat transfer medium are deteriorated. Therefore, on these reaction tubes, there is increased possibility of formation of a part where the heat transfer is deteriorated between these reaction tubes and the heat transfer medium. Herein, according to the present invention, a thermometer is provided to such reaction tube to form a temperature-measuring reaction tube. Data of the temperature measured by the temperature-measuring reaction tube is utilized. Therefore, the multi-tubular reactor can be designed or produced wherein the condition in the shell can be appropriately controlled so as to prevent any formation of hot spot or cold spot.

According to the eleventh invention, even in case of the substance is produced by a gas-solid heterogeneous reaction, a multi-tubular reactor can be designed or produced wherein the condition in the shell can be appropriately controlled not to form any hot spot or cold spot.

According to the twelfth invention, although the reaction generating (meth)acrolein and/or (meth)acrylic acid is an exothermic reaction, a multi-tubular reactor can be designed or produced wherein the condition in the shell can be appropriately controlled not to form any hot spot.

According to the thirteenth invention, even in case of the diameter of the shell is large, a multi-tubular reactor can be designed or produced wherein the reaction proceeding in the reaction tube can be exactly monitored so that the condition in the shell can be appropriately controlled.

According to the fourteenth invention, even in case of a lot of reaction tubes are provided, a multi-tubular reactor can be designed or produced wherein the condition in the shell can be appropriately understood by a small number of the thermometers. Herein, the number of the thermometers provided to the reaction tubes can be reduced. Therefore, setting up the reactor for its operation can be carried out in a short time in case of the number of the reaction tubes is large. Herein, structure of the multi-tubular reactor is not to be complicated in comparison with the case a large number of the thermometers are provided.

According to the fifteenth invention, when the heat transfer medium is supplied into the shell, a multi-tubular reactor can be designed or produced wherein flow resistance of the heat transfer medium can be decreased, and the contacting condition between the heat transfer medium and the reaction tubes can be improved.

According to the sixteenth invention, a multi-tubular reactor can be designed or produced wherein the heat transfer medium can flow in the shell, the heat transfer medium can contact with the reaction tube, and the flowing condition of the heat transfer medium, and the contacting efficiency with the reaction tube, and heat transfer can be improved.

According to the seventeenth invention, a multi-tubular reactor can be designed or produced wherein the reaction occurring in the reaction tube can be appropriately controlled so that the temperature difference between any locations in the axial direction of the reaction tube can be decreased even in case of the reaction tube is longer.

According to the eighteenth invention, the flow of the heat transfer medium is symmetry about an axis, the same flowing condition pattern can be repeated about the central axis of the shell every 30 degree. Therefore, by allocating the temperature-measuring reaction tube(s) to an area every 30 degree in a cross section of the shell, the entire reaction condition in the reactor can be understood. Therefore, a multi-tubular reactor can be designed or produced wherein the condition in the shell can be appropriately determined. Thus, according to the eighteenth invention, the number of the temperature-measuring reaction tubes can be further reduced.

DESCRIPTION OF EMBODIMENTS

Figure 1:
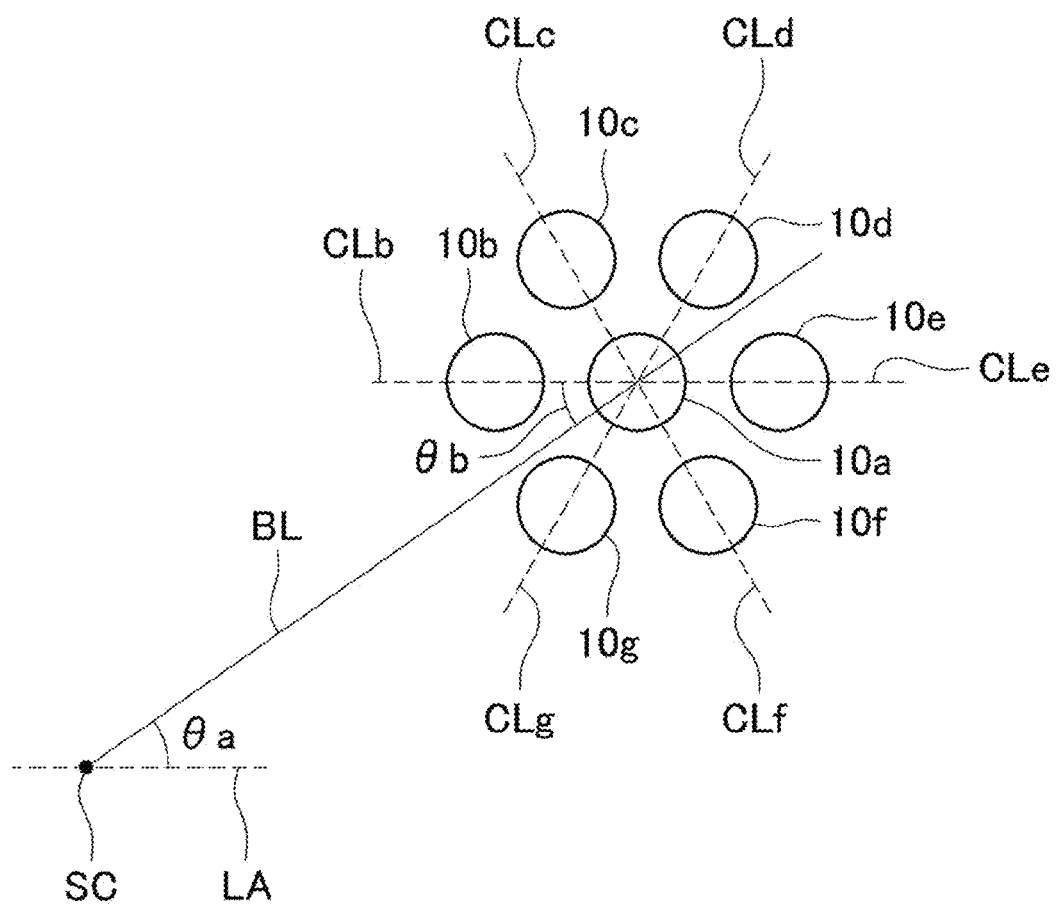
FIG. 1 is a schematic explanation view of a method for setting a temperature-measuring reaction tube in a multi-tubular reactor according to the present invention.

One embodiment of the multi-tubular reactor according to the present invention is described in detail with referring to the appended drawings. The multi-tubular reactor according to the present invention is not limited to the embodiments illustrated in the appended drawings.

The multi-tubular reactor according to the present invention is characterized in that the multi-tubular reactor, preferably a fixed-bed multi-tubular reactor, wherein a raw material(s), preferably a fluid raw material(s), more preferably a gaseous raw material(s) can be subjected to a reaction in a plurality of reaction tubes located in the cylindrical shell to produce an object substance(s) so that the formation of any hot spot or cold spot on the reaction tubes can be prevented.

Herein, the hot spot means a part where the temperature is increased on the reaction tube in comparison with the other part of the reaction tube, in case of that the reaction where the object substance(s) is/are produced from the raw material(s) is an exothermic reaction.

Herein, the cold spot means a part where the temperature is decreased on the reaction tube in comparison with the other part of the reaction tube, in case of that the reaction where the object substance(s) is/are produced from the raw material(s) is an endothermic reaction.

Hereinafter, a typical example of the multi-tubular reactor according to the present invention is explained, which is, for example, a fixed-bed multi-tubular reactor which can produce the object substance(s) by a gas-solid heterogeneous reaction.

Herein, the object substance which can be produced in the multi-tubular reactor according to the present invention includes, for example, (meth)acrolein (or (meth)acrylic aldehyde) and/or (meth)acrylic acid. For example, the (meth)acrolein and/or (meth)acrylic acid can be produced by supplying propylene, isobutylene, t-butyl alcohol, or a mixture of two or more thereof, preferably in a gaseous state, in the reaction tubes of the multi-tubular reactor according to the present invention; and oxidizing it in the gas phase with a gas containing molecular oxygen.

Specifically, propylene can be oxidized to form acrolein (or acrylic aldehyde), and further oxidized to form acrylic acid. Isobutylene can be oxidized to from methacrolein (or methacrylic aldehyde), and further oxidized to form methacrylic acid. t-Butyl alcohol can be oxidized to form methacrolein, via isobutylene, and further oxidized to from methacrylic acid.

Herein, (meth)acrolein and/or (meth) acrylic acid can be produced by a reaction of the above-described raw material (preferably a raw material gas) in the reaction tube. At that time, heat may be generated. However, according to the multi-tubular reactor of the present invention, the condition in the shell can be appropriately controlled so that the hot spot cannot be formed.

Herein, according to the present invention, reactants such as propylene, isobutylene, t-butyl alcohol, or a mixture of two or more thereof, and materials which can participate in the reaction such as a gas containing molecular oxygen may be generally referred to as a "raw material", or a "raw material gas" in case of a gas.

Herein, as the reaction which can be carried out in the multi-tubular reactor according to the present invention, an exothermic reaction can be carried out, and an endothermic reaction such as a steam reforming of methane ($CH_4 + H_2O \rightarrow CO + 3H_2$), and the like, can be carried out, but the reaction which can be carried out in the present invention is not particularly limited thereto.

Figure 2:
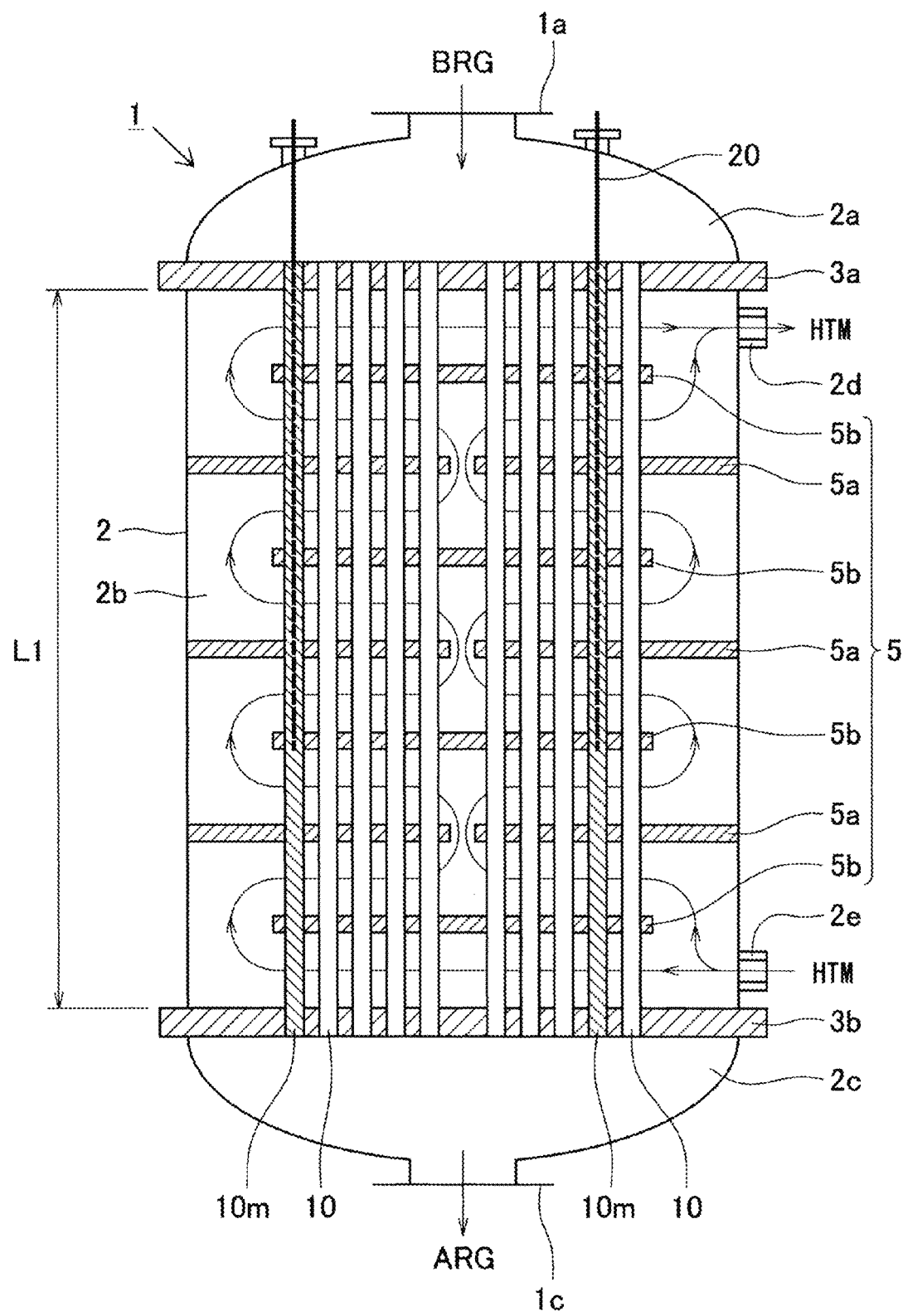
FIG. 2 is a schematic explanation view of a multi-tubular reactor according to the present invention.

Before describing the features of the multi-tubular reactor according to the present invention, initially, basic structure of the multi-tubular reactor according to the present invention is briefly described with referring to FIG. 2.

In FIG. 2, in order to facilitate the understanding of the structure of the multi-tubular reactor according to the present invention, it is conveniently described so that the number of the reaction tubes may be greatly reduced in comparison to that of the actual multi-tubular reactor. It is also conveniently described so that the relative dimension in each component may be different from that of the actual multi-tubular reactor.

The multi-tubular reactor 1 according to the present invention as shown in FIG. 2 is a reactor wherein a plurality of reaction tubes 10 are located in a cylindrical shell 2, wherein one or more of disk-and-doughnut type baffle(s) 5 is/are provided as a baffle board(s) which can control a flow of a heat transfer medium flowing in the shell 2 (hereinafter, which may be abbreviated as a "HTM (Heat Transfer Medium)").

Specifically, as shown in FIG. 2, the multi-tubular reactor 1 comprises a hollow cylindrical shell 2. A plurality of reaction tubes 10 are accommodated in the shell 2. For example, the shell 2 can accommodate 5000 or more, preferably 5000 to 100000, more preferably 10000 to 60000 of the reaction tubes 10.

The material forming the shell 2 is not particularly limited. For example, the shell 2 can be comprised of a material such as stainless, carbon steel and nickel.

Figure 3:
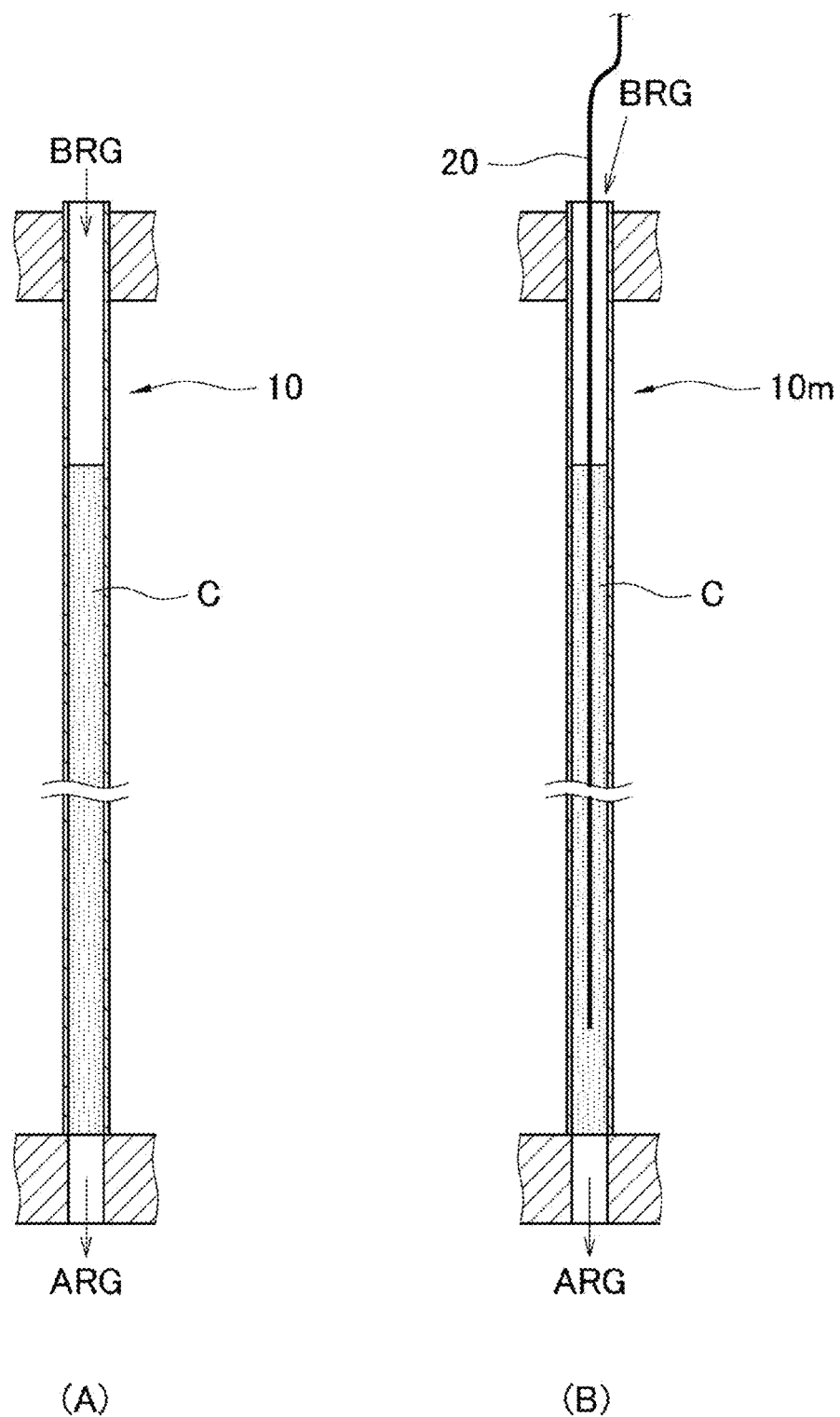
FIG. 3(A) is a schematic explanation view of a normal reaction tube located in a shell of a multi-tubular reactor according to the present invention, and (B)
FIG. 3(B) is a schematic explanation view of a temperature-measuring reaction tube.

As shown in FIG. 3, for example, a plurality of the reaction tubes 10 to be located in the shell 2 may be comprised of a material such as stainless, carbon steel and nickel. Each of a plurality of the reaction tubes 10 is a straight circular tube, which can be allocated so that the central axis (i.e., an axis extending from a geometrical center of a cross section in a perpendicular direction to the longitudinal direction of the reaction tube, and extending in a perpendicular direction to the cross section) is in parallel with the central axis of the shell 2 (i.e., an axis extending from a geometrical center of the shape (e.g., a canter of a circle) on a cross section in a perpendicular direction to the longitudinal direction of the cylindrical shell, and extending in a perpendicular direction to the cross section). Herein, among the plurality of the reaction tubes 10, at least one reaction tube 10 is provided with a thermometer 20. The thermometer 20 can measure a temperature inside the reaction tube 10. Thereby, conditions in the shell 2 can be determined (see FIG. 3 (B)).

As shown in FIG. 2 and FIG. 3, according to the present invention, a reaction tube 10 provided with a thermometer 20 therein may be referred to as a "temperature-measuring reaction tube (10m)". As long as the temperature inside the reaction tube 10 can be measured, particularly as long as the temperature in the reaction system can be measured, any location in the reaction tube 10 where the thermometer 20 is provided is not particularly limited.

Herein, according to the present invention, simply, the reaction tube 10 and the temperature-measuring reaction tube 10m may be generally referred to as a reaction tube or a reaction tube 10.

Herein, as shown in FIG. 3, a catalyst C suitable for the object reaction may be optionally filled in the reaction tube 10 in a given amount.

For example, in case of a raw material gas (hereinafter, which may be also referred to as "BRG") may be subjected to a reaction to produce an object substance without any catalyst mediation, the catalyst C may be present or absent in the reaction tube 10. Herein, in case of the catalyst C is present in the reaction tube 10, the amount to be used is not particularly limited, but it can be appropriately determined depending on the kind and amount of the raw material as well as the object reaction and the object product.

The catalyst C can be appropriately determined depending on the raw material to be used as well as the object reaction and the object product. For example, in a gas-solid heterogeneous reaction, a molybdenum metal-based catalyst or the like can be used, as a catalyst, in a solid state, for example, in case of that propylene, isobutylene, t-butyl alcohol, or a mixture of two or more thereof is oxidized in a gaseous phase with a gas containing molecular oxygen to produce (meth)acrolein and/or (meth)acrylic acid, In case of steam reforming of methane, a nickel metal-based catalyst, a ruthenium metal-based catalyst, or the like, can be used as a catalyst.

Herein, the catalyst which can be used in the present invention is not limited to those described above.

According to the present invention, the "gas-solid heterogeneous reaction" means a heterogeneous reaction between a gaseous phase and a solid phase. More specifically, it means that a raw material gas as a gas phase such as the above-described propylene, isobutylene, t-butyl alcohol, or a mixture of two or more thereof, and a gas containing molecular oxygen, contacts and reacts on the catalyst (as the solid phase) filled in the reaction tube. Herein, according to the present invention, the catalyst filled in the reaction tube 5 or the reaction tube in which the catalyst is filled is referred to as a "fixed bed".

As shown in FIG. 2, a plurality of the reaction tubes 10 to be located in the shell 2 can be held at their both ends by a pair of holding plates 3a, 3b. A pair of the holding plates 3a, 3b can divide the inner space of the shell 2 into three spaces 2a, 2b and 2c in air-tight and liquid-tight state. A pair of the holding plates 3a, 3b can be provided at any locations in a direction along the central axis of the shell 2 so that the reaction tubes 10 can independently communicates to the space 2a and the space 2c at their both opening ends, respectively. Herein, the opening ends of the reaction tube 10 may be independently protruded from the holding plates 3a, 3b towards the space 2a, 2c, respectively. The opening ends may be inside the holding plates 3a, 3b. The opening ends of the reaction tube 10 may be flush with the holding plates 3a, 3b, respectively, at the side directing to the space 2b. Alternatively, the opening ends may be flush with the holding plates 3a, 3b, respectively, at the side directing to the spaces 2a, 2c, respectively, passing through the holding plates 3a, 3b, respectively. Herein, as shown in FIG. 2, the holding plates 3a, 3b may have holes through which a plurality of the reaction tubes 10 are passed.

As shown in FIG. 2, the shell 2 can be further provided with a supply port 1a communicating the space 2a to the outside thereof, and an exhaust port 1c communicating the space 2c to the outside thereof.

The supply port 1a can be provided for supplying, for example, a raw material gas (BRG) to the space 2a.

The exhaust port 1c can be provided for discharging the object substance generated by the reaction of the raw material gas (BRG) in the reaction tube 10 (hereinafter, which is also referred to as a "ARG").

According to such structure, the raw material gas (BRG) which can be supplied through the supply port 1a is passed through the reaction tubes 10 and 10m, and the object substance (ARG) produced in the reaction tubes 10 and 10m can be discharged through the exhaust port 1c.

Herein, as shown in FIG. 2, the shell 2 may be provided with a heat transfer medium-supplying port 2e for supplying a heat transfer medium (HTM) such as fused salt (HTS) such as sodium nitrite and potassium nitrate into the space 2b; and a heat transfer medium-exhausting port 2d for discharging, from the space 2b, the heat transfer medium (HTM) supplied from the heat transfer medium-supplying port 2e. The heat transfer medium-supplying port 2e can be provided on the side oriented to the holding plate 3b dividing the inner space to the space 2b and the space 2c, preferably neighboring to the holding plate 3b, more preferably adjacent or adjoining to the holding plate 3b, or at a bottom area of the side wall of the shell 2 in the space 2b. The heat transfer medium-exhausting port 2d can be provided on the side oriented to the holding plate 3a dividing the inner space to the space 2a and the space 2b, preferably neighboring to the holding plate 3a, more preferably adjacent or adjoining to the holding plate 3a, or at a top area of the side wall of the shell 2 in the space 2b. Accordingly, the heat transfer medium-supplying port 2e and the heat transfer medium-exhausting port 2d can be provided so that in case of that a heat transfer medium (HTM) is supplied into the space 2b from the heat transfer medium-supplying port 2e, the space 2b can be filled with the heat transfer medium (HTM), and the heat transfer medium (HTM) can flow in a direction along the axis of the reaction tube 10 from the side of the holding plate 3b toward the side of the holding plate 3a, and discharged from the heat transfer medium-exhausting port 2d.

Herein, one or more of disk-and-doughnut type baffle(s) 5 (hereinafter, which may be abbreviated as a "baffle 5", or simply "baffle") is/are provided in the space 2b of the shell 2. The baffle 5 includes, but is not particularly limited to, conventionally known disk-and-doughnut type baffles. For example, as shown in the figures, two or more of the baffles having different shapes from each other may be used in a combination.

More specifically, as shown in FIG. 2, for example, a baffle 5a in an annular shape having a single through-hole at the center part (or in a so-called doughnut shape) (hereinafter, which may be abbreviated as a "baffle 5a") and a baffle 5b in a disk shape having a diameter in a dimension larger than that of the through-hole provided at the center part of the baffle 5a (hereinafter, which may be abbreviated as a "baffle 5b") are used in a combination as the disk-and-doughnut type baffle 5. Herein, such reactor may be referred to as a disk-and-doughnut type reactor.

Herein, the baffle 5a and the through-hole thereof as well as the baffle 5b can be provided so that their central axes (each of which is an axis extending from a geometrical center of a cross-section thereof which is in parallel with the plane of the baffle (generally which is a center of a circle), and extending in a direction perpendicular to the plane of the baffle) may be aligned coaxially with the central axis of the shell 2. Both of the baffles 5a and 5b may be provided along the central axis direction of the shell 2 and alternately arranged. Herein, when a plurality of the baffles are provided in this way, the interval between them is not particularly limited.

The baffle 5a is that having a through-hole provided at the center part through which a heat transfer medium (HTM) can be passed.

Herein, the baffle 5a has an outer diameter approximately same to the inner diameter of the shell 2, or smaller than the inner diameter.

Herein, the through-hole provided at the center part of the baffle 5a has a dimension which is not particularly limited as long as the heat transfer medium (HTM) can be passed therethrough.

The baffle 5b is that having a diameter in a dimension larger than that of the through-hole of the baffle 5a. The heat transfer medium (HTM) can be passed about the periphery of the baffle 5b. Therefore, the baffle 5b has a diameter (i.e., outer diameter) in a dimension smaller than the inner diameter of the shell 2.

Herein, the baffle 5b has a diameter which is not particularly limited in its dimension as long as the heat transfer medium (HTM) can be passed about the periphery thereof.

A ratio of the diameter of the through-hole of the baffle 5a to the diameter of the baffle 5b (Diameter of the through-hole of the baffle 5a:Diameter of baffle 5b) is not particularly limited, but, for example, it is from 1:1.1 to 1:20, preferably from 1:2 to 1:3.

Herein, a plurality of the reaction tubes 10 can be provided through the holes, each of which has a dimension approximately same to the outer diameter of the reaction tube provided at the baffle such as baffles 5a and 5b, in the shell 2, or has a dimension larger than the outer diameter of the reaction tube. In case of the baffle 5a is provided, any reaction tube 10 is not provided in the through-hole at the center part of the baffle 5a.

Thus, in the shell 2, a plurality of the reaction tubes 10 cannot be provided in the through-hole at the center part of the baffle 5a. All the reaction tubes 10, however, can be provided through the holes for these reaction tubes, which are provided at any locations excluding the position of the through-hole at the center part of the baffle 5a.

The baffles which can be used in the present invention are not limited to the above-described baffles 5a and 5b. Herein, kind, combination, shape and allocation of the baffle are not particularly limited. They can be appropriately determined depending on the raw material to be used, the object reaction, and the object product.

Herein, according to the present invention, the number of the baffles 5 provided in the shell 2 is not particularly limited. It may be appropriately determined depending on the raw material to be used, the object reaction, and the object product. For example, it is from 1 to 50, preferably from 2 to 10, more preferably from 3 to 6.

Thickness of the baffle to be used in the present invention is not particularly limited. It may be appropriately determined depending on the raw material to be used, the object reaction, and the object product. For example, it is from 0.1 to 5 mm, preferably from 0.5 to 3 mm, more preferably from 1 to 2 mm.

Material for the baffle to be used in the present invention is not particularly limited. It may be appropriately determined depending on the raw material to be used, the object reaction, and the object product. For example, it is able to use a baffle comprised of a material such as stainless, carbon steel and nickel.

Herein, a method for providing the baffle to be used in the present invention to the shell 2 is not particularly limited. The baffle may be provided by appropriately using a conventionally known method for the installation.

The multi-tubular reactor according to the present invention may have such structure. Therefore, when the heat transfer medium (HTM) which may be flowed in the space 2b of the shell 2 is passed on one or more of the baffles 5 comprising, for example, the baffle 5a and/or 5b, the direction of the flow of the heat transfer medium may be changed to a direction crossing the central axis of the shell 2 (or perpendicularly or transversely to the central axis of the shell 2).

Specifically, as shown in FIG. 2, the heat transfer medium (HTM) passed through the through-hole provided at the center part of the baffle 5a positioned downwardly may produce a flow in a radial direction outwardly directing to the inner wall surface of the shell 2 from the central axis of the shell 2 in order to pass through a space between the outer periphery of the baffle 5b positioned upwardly relative to the baffle 5a and the inner wall surface of the shell 2.

Similarly, as shown in FIG. 2, the heat transfer medium (HTM) passed through the space between the outer periphery of the baffle 5b positioned downwardly and the inner wall surface of the shell 2 may produce a flow in a radial direction of the shell 2 inwardly directing to the central axis from the inner wall surface of the shell 2 in order to pass through the through-hole provided at the center of the baffle 5a positioned upwardly relative to the baffle 5b. Therefore, for example, as shown in FIG. 2, the provision of a plurality of the baffles 5 comprising the baffles 5a and 5b can allow the heat transfer medium (HTM) to be contacted with the reaction tubes 10 in a direction crossing the central axis (or perpendicularly or transversely to the central axis) (desirably, in a direction perpendicular to a longitudinal direction of the reaction tube) toward the reaction tube 10. Accordingly, the contacting efficiency between the reaction tubes 10 and the heat transfer medium (HTM) can be further improved and the heat exchange efficiency between them can be improved in comparison with the case where the heat transfer medium (HTM) is flowing in a direction along the axis of the reaction tube 10.

Herein, according to the multi-tubular reactor 1 of the present invention, one baffle 5b can be provided beside the holding plate 3b, and the other baffle 5b can be provided beside the holding plate 3a, as shown in FIG. 2, in order to control the flow of the heat transfer medium (HTM) to the heat transfer medium-exhausting port 2d from the heat transfer medium-supplying port 2e. Herein, the efficiencies of the flow and diffusion of the heat transfer medium (HTM) to the inner space 2b are improved. Furthermore, by providing a plurality of the baffles 5a and 5b alternately between two baffles 5b provided beside the holding plates 3a and 3b, respectively, the contacting efficiency between the reaction tubes 10 and the heat transfer medium (HTM) is further improved.

For example, the multi-tubular reactor 1 according to the present invention may have such structure described above. Therefore, in case of that, for example, a raw material gas (BRG) is supplied to the space 2a of the shell 2 from the supply port 1a, the raw material gas (BRG) can be supplied inside each of the reaction tubes 10, and the raw material gas (BRG) can be flowed in the reaction tube 10 in one direction toward the space 2c. In the reaction tube 10, the raw material gas (BRG) can be optionally contacted with the catalyst in order to be subjected to a reaction to produce the object substance. Through the space 2c, the produced object substance (ARG) can be discharged from the exhaust port 1c to the outside thereof.

Herein, by supplying a heat transfer medium (HTM) into the space 2b in the shell 2 from the heat transfer medium-supplying port 2e, the reaction tubes 10 and the heat transfer medium (HTM) can be efficiently contacted with each other. Therefore, heat generated during the reaction of the raw material gas (BRG) can be thermally removed by the heat transfer medium (HTM), and a quantity of heat required for the reaction can be provided to the raw material gas (BRG) from the heat transfer medium (HTM).

Herein, according to the present invention, one or more of the baffle(s) 5 is/are provided in the space 2b. Therefore, the heat transfer medium (HTM) can be efficiently contacted with the reaction tubes 10, and removal or addition of the heat can be further efficiently carried out by the heat transfer medium (HTM).

Herein, the reaction tube 10 may be a straight tube, but it is not limited to a circular tube necessarily having a circular cross section. For example, it may be a tube having a triangular or rectangular cross section. Herein, dimension of the reaction tube 10 (such as size, diameter or longitudinal length in the cross section) is not particularly limited. It may be appropriately determined depending on the raw material, the object reaction, and the object product.

(Arrangement of a Plurality of Reaction Tubes 10)

As specifically explained in the above-described embodiment, the heat transfer medium (HTM) can be flowed in the shell 2, particularly in the space 2b of the shell 2, in a radial direction of the shell 2 outwardly and/or inwardly so as to have a desired velocity component by providing the disk-and-doughnut type baffle(s) 5, in the multi-tubular reactor 1 of the present invention.

In order to improve the contacting efficiency and improve the heat exchange efficiency between the heat transfer medium (HTM) which may have such flow and a plurality of the reaction tubes 10, a plurality of the reaction tubes 10 to be located in the shell 2 is allocated so as to have a cross section of a triangular configuration, relative to the flow of the heat transfer medium (HTM), in the multi-tubular reactor 1 of the present invention.

Figure 4:
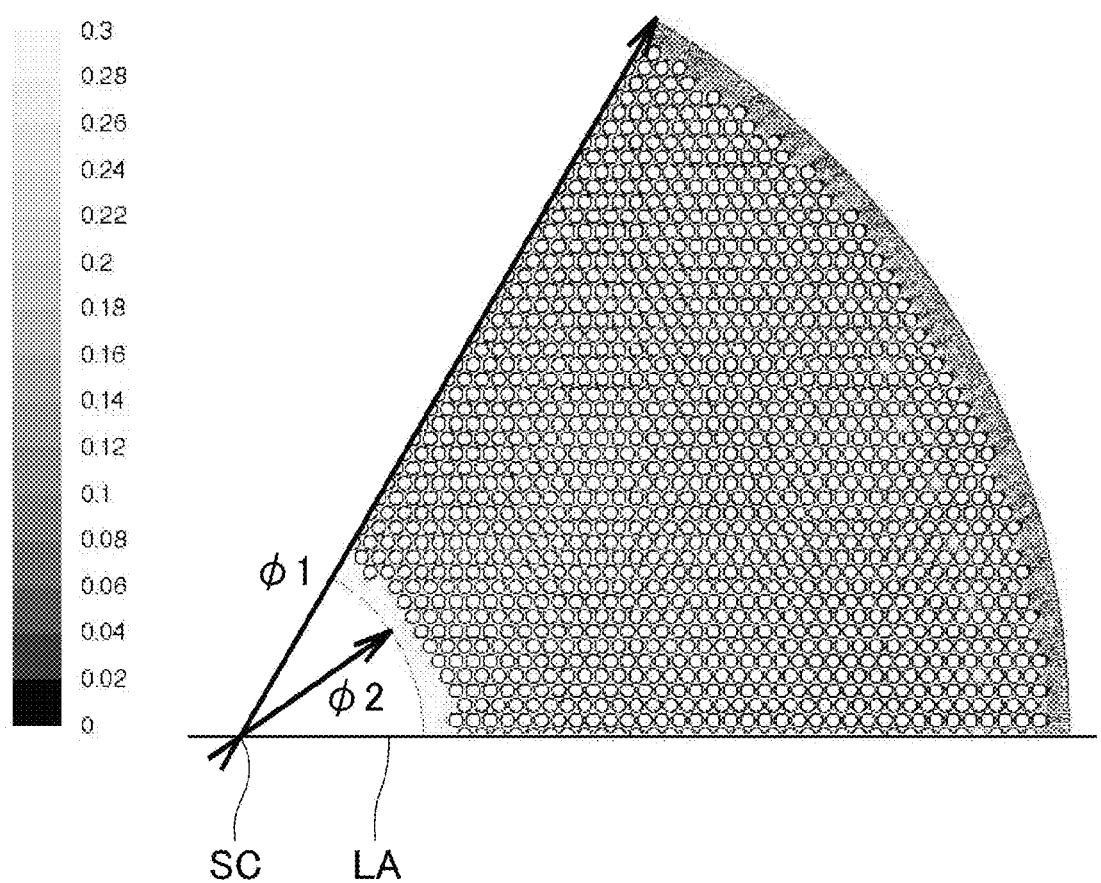
FIG. 4 is a schematic explanation view of a model to which numerical simulations are carried out in the examples.

In the present invention, the "triangular configuration" means an arrangement having a pattern as shown in FIG. 4 in a cross section of the shell 2 (or a cross section of the multi-tubular reactor 1 of the present invention perpendicular to the central axis of the shell 2). The pattern shown in FIG. 4 has units, each of which has three adjacent reaction tubes, wherein it is characterized in that the central axes of these three reaction tubes are located at three summits of a virtual equilateral triangle, respectively.

Herein, according to the present invention, a pitch between the reaction tubes (i.e., a distance between the central axes of the reaction tubes next to each other) is not particularly limited. For example, it is within a range from 1.1 to 1.5 times of the outer diameter of the reaction tube, preferably from 1.2 to 1.3 times of the outer diameter of the reaction tube.

Herein, the arrangement of the reaction tubes used in the present invention includes an arrangement such as a "triangular zigzag arrangement".

Accordingly, in case of that a plurality of the reaction tubes 10 are arranged in the triangular configuration in the shell 2, the reaction tubes 10 can be arranged so as to be in a rotational symmetry around the central axis of the shell 2.

Accordingly, for example, when the heat transfer medium (HTM) flows outwardly and/or inwardly along the radial direction from/to the central axis of the shell 2, i.e., when the baffles 5 are provided therein as shown in the multi-tubular reactor 1 of the present invention, it can be considered that the heat transfer medium (HTM) has almost the same flowing condition at the circumferential direction of the shell 2.

However, the present inventors understand that the flow condition of the heat transfer medium (HTM) is varied at the circumferential direction of the shell 2, and therefore the individual reaction tube 10 has different heat transferring ability, even if a plurality of the reaction tubes 10 are provided in the triangular configuration in the shell 2 of the multi-tubular reactor 1 and the disk-and-doughnut type baffles 5 are provided therein.

Herein, based on such understanding that the flow condition of the heat transfer medium (HTM) is varied at the circumferential direction of the shell 2, the multi-tubular reactor 1 of the present invention is characterized in that a thermometer 20 for determining the reaction condition in the reaction tube 10 is provided at a location where the heat transfer is relatively deteriorated.

Accordingly, in case of the data of the temperature which can be measured by such thermometer 20 is utilized, the condition in the shell 2 can be appropriately controlled so that any formation of the hot spot or the cold spot can be prevented.

Hereinafter, the location where the thermometer 20 is provided, i.e., the reaction tube in which the thermometer is located (hereinafter, which is referred to as a "temperature-measuring reaction tube (10*m*)") is described in detail.

According to the present invention, as specifically shown in FIG. 1, the temperature-measuring reaction tube can be determined as follows.

Initially, in a cross section of the multi-tubular reactor 1, which is perpendicular to the central axis of the shell 2, a line through a central axis of any one reaction tube 10*a* (an axis extending form the geometrical center of the cross section perpendicular to the longitudinal direction of the reaction tube 10*a* (which is center of circle shown in the figure), and extending in a direction perpendicular to the cross section) and the central axis of the shell 2 (an axis extending from the geometrical center of the cross section perpendicular to the longitudinal direction of the shell 2 (generally, which is center of circle), and extending in a direction perpendicular to the cross section, hereinafter which axis is abbreviated as "SC") is determined. Hereinafter, this line is referred to as a "base line (BL)".

On this cross section, a line through the central axis of the reaction tube 10*a* and each central axis of at least one reaction tube next to the reaction tube 10*a* (hereinafter, which is referred to as an "adjacent reaction tube (10*b* to 10*g*)") (an axis extending from the geometrical center of the cross section perpendicular to the longitudinal direction of each reaction tube (which is center of circle in the example shown in the figure), and extending in a direction perpendicular to the cross section) is determined. Hereinafter, this line is referred to as a "connect line (CLb to CLg)".

According to the present invention, in convenience of the explanation, the reaction tube next to the reaction tube 10*a* in FIG. 1 is referred to as an "adjacent reaction tube". The reaction tube 10*a* and the adjacent reaction tube are not directly or physically contacted with each other.

In the present invention, a plurality of the reaction tubes 10 located in the shell 2 are not directly or physically contacted with each other.

Herein, as shown in FIG. 1, an angle between the base line BL and each of the connect lines CLb to CLg is defined as angles θb to θg, respectively. Hereinafter, the angles (θb to θg) are referred to as "adjacent angles (θb to θg)".

In the present invention, degree of each adjacent angle (θb to θg) is conveniently indicated as a degree of an angle between the base line BL and each of the connect lines (CLb to CLg) within a range from 0 to 90° (i.e., the degree of the angle between the base line BL and the connect line CL is indicated as the degree of the adjacent angle by measuring the degree of the smallest angle (i.e., in an acute angle) among the angles which can be formed).

Herein, as shown in FIG. 1, in case of a single line LA crossing over the central axis (SC) of the shell 2 is optionally determined, if degree of angle θa between the line LA and the base line BL is varied, degree of each adjacent angle (θb to θg) may be correspondingly varied. Therefore, depending on the location of the reaction tube 10*a*, possible degree of each adjacent angle (θb to θg) may be correspondingly varied as well.

Accordingly, in the multi-tubular reactor 1 of the present invention, the reaction tube 10*a* is provided with the thermometer 20 to form a temperature-measuring reaction tube if the reaction tube 10*a* has at least one adjacent reaction tube having an angle within a range from 0 to 15 degree as the degree of the adjacent angle (θb to θg).

Namely, a reaction tube having at least one adjacent reaction tube is provided with a thermometer to form a temperature-measuring reaction tube wherein the degree of the angle (θb to θg) between the base line BL and each of the connect lines (CLb to CLg) is within a range from 0 to 15 degree (°) with respect to the adjacent reaction tube. Accordingly, in the embodiment shown in FIG. 1, if degree of at least one adjacent angle (θb to θg) is within a range from 0 to 15 degree, the reaction tube 10*a* is provided with a thermometer, and this reaction tube 10*a* can be the temperature-measuring reaction tube 10*m*.

According to the present invention, at least one reaction tube satisfying with the requirements with respect to the above-described adjacent angle can be provided with a thermometer to from the temperature-measuring reaction tube. Therefore, there is no need to provide thermometers to all the reaction tubes.

At the location of such temperature-measuring reaction tube $10m$, degree of at least one adjacent angle is within a range from 0 to 15 degree. Therefore, the contacting efficiency between the temperature-measuring reaction tube $10m$ and the heat transfer medium (HTM) may be deteriorated. Namely, according to the present invention, the reaction tube 10 with possible formation of a part having deteriorated heat transfer between the reaction tube and the heat transfer medium (HTM) in a high possibility is selected among the plurality of the reaction tubes 10 located in the shell 2 to provide the temperature-measuring reaction tube $10m$.

For example, around the temperature-measuring reaction tube $10m$ having an adjacent reaction tube having the degree of the adjacent angle being 0 degree, the adjacent reaction tube can be present on the base line BL. Therefore, between the adjacent reaction tube and the temperature-measuring reaction tube $10m$, a part (or a pool) with the flow of the heat transfer medium (HTM) being very slow in the radial direction can be presented.

Whereas, between the other adjacent reaction tube (particularly, adjacent reaction tube having more than 15 degree of the adjacent angle, preferably adjacent reaction tube having more than 20 degree of the adjacent angle) and the temperature-measuring reaction tube $10m$, the flow of the heat transfer medium (HTM) can be rectified in the radial direction, and the flow rate of the heat transfer medium (HTM) can be increased in the radial direction.

In this manner, around the temperature-measuring reaction tube $10m$, there is an adjacent reaction tube having the degree of the adjacent angle being within a range of from 0 to 15 degree. Therefore, efficiency of the heat transfer with the heat transfer medium (HTM) may be deteriorated, and the sufficient removal or addition of the heat by the heat transfer medium (HTM) cannot be carried out. Accordingly, hot spot or cold spot may be easily formed.

Based on these aspects, if data of the temperature which can be measured at such temperature-measuring reaction tube $10m$ is utilized, and if the flow of the heat transfer medium (HTM) or the like is controlled so that the temperature at the temperature-measuring reaction tube $10m$ is in an appropriate temperature, the formation of hot spot or cold spot can be prevented. Namely, according to the present invention, at the temperature-measuring reaction tube $10m$ where the hot spot or cold spot may be easily occurred, such occurrence of the hot spot or cold spot can be prevented. Therefore, at the other reaction tube than the temperature-measuring reaction tube $10m$, occurrence of the hot spot or cold spot can be sufficiently prevented as well.

Accordingly, in comparison with the case where the temperature is measured without considering the ununiformity of the heat transferring ability, the condition inside the space $2b$ of the shell 2 can be appropriately controlled, according to the present invention, since there is no need to control the condition based on the surplus estimation of the risk of the occurrence of the hot spot or cold spot.

According to the multi-tubular reactor 1 of the present invention, the flow of the heat transfer medium (HTM) in the space $2b$ of the shell 2 is symmetry around the axis, as it is described above, since at least one baffle 5 is provided. Therefore, even in case of the number of the temperature-measuring reaction tubes $10m$ is decreased, the condition in the shell 2 can be appropriately determined.

Namely, on a cross section of the multi-tubular reactor 1, which is perpendicular to the longitudinal central axis of the shell 2, a situation where the same flowing condition pattern can be repeated about the central axis of the shell every 30° is provided. Therefore, if the temperature condition can be understood at any one 30° area on the cross section, it is possible to approximately understand the entire reaction condition of the multi-tubular reactor 1.

Herein, by the method according to the present invention, the number of the temperature-measuring reaction tubes $10m$ can be decreased since at least one temperature-measuring reaction tube $10m$ may be set only at any 30° area.

Accordingly, the apparatus structure of the multi-tubular reactor 1 can be simplified, and the number of the steps for the maintenance thereof can be decreased, and safety operation can be managed in comparison with the case where the temperature-measuring reaction tubes $10m$ are conventionally provided all over the cross section.

(Number of Reaction Tubes 10)

According to the multi-tubular reactor, the number of the reaction tubes which can be located in the shell is significantly varied depending on the apparatus. However, in the multi-tubular reactor having, for example, 5000 or more, and particularly 10000 or more of the reaction tubes, it is preferable that the reaction tube 10 determined according to the method as described above is provided with a thermometer 20 to form the temperature-measuring reaction tube $10m$.

If very large number, or 5000 or more of the reaction tubes 10 are provided, there may be a case the flow of the heat transfer medium (HTM) in the shell 2 may be ununiform since the shell diameter (and inner diameter) of the shell 2 is increased. Thereby, the temperature of the reaction tube may be ununiform, and difference between the temperatures of the reaction tubes 10 may be increased as well. Therefore, in order to understand the conditions in the shell 2, conditions where the temperatures are ununiform among the reaction tubes 10 should be understood. To do so, provision of a great number of the thermometers 20 is required. However, in that case, the apparatus structure of the multi-tubular reactor 1 would be complicated, and cost of the equipment would be increased, and steps for the maintenance would be increased, and burden on the maintenance would be increased.

Herein, according to the method of the present invention, the conditions where the temperatures are ununiform can be exactly understood and detected, among the reaction tubes 10, if the thermometer 20 is provided, even in case where the number of the provided thermometers 20 is reduced.

(Number of Temperature-Measuring Reaction Tubes $10m$)

In the multi-tubular reactor 1 according to the present invention, the number of the temperature-measuring reaction tubes $10m$ to be provided (i.e., the number of the reaction tubes 10 in which the thermometer 20 is to be provided) is desirably decreased, preferably 3% or less, and more preferably 1% or less, relative to the number of the all reaction tubes 10. For example, in case of the number of the reaction tubes 10 is about 10000, when the number of the temperature-measuring reaction tubes $10m$ is at least about 10, the conditions in the shell 2 can be sufficiently understood and controlled.

Herein, in case of the ideal condition, i.e., when the multi-tubular reactor 1 has no manufacturing error, and the flow of the heat transfer medium (HTM) is in a constant amount, and catalyst packing amount, packing density and gas flow are uniform in each reaction tube 10, the thermometer 20 is provided in the reaction tube 10 with the formation of the hot spot or cold spot being most probably occurred (i.e., a reaction tube 10 having an adjacent reaction tube wherein the degree of the angle between the base line BL and the connect line CL is within a range from 0 to 15 degree) in the 30° area on a cross section of the multi-tubular reactor, which is perpendicular to the longitudinal direction of the shell 2. In this area, even if the number of the temperature-measuring reaction tube 10m is only one, operation of the multi-tubular reactor 1 can be appropriately controlled as well.

Although the length of the reaction tube 10 is varied, it is preferable that a part thereof where the heat transfer medium (HTM) supplied in the shell 2 contacts with the reaction tube has a length (L1) of 1.3 m or more. According to such length L1 (1.3 m or more) of the part where the heat transfer medium (HTM) contacts with the reaction tube (see FIG. 2, L1 corresponds to the height (length) of the space 2b of the shell 2 in the embodiment of FIG. 2), the shell diameter can be decreased, and ununiformity of the flow of the heat transfer medium (HTM), i.e., unevenness among the temperatures of the reaction tubes 10 can be reduced, even if total amount of the catalyst filled in the multi-tubular reactor 1 is the same amount. Furthermore, depending on the temperature measured at the temperature-measuring reaction tube 10m, the temperature of the reaction tube or the heat transfer medium can be controlled, and thereby the reaction proceeding in the reaction tube 10 (i.e., operation of the multi-tubular reactor 1) can be appropriately controlled.
(Regarding Shell 2)

According to the multi-tubular reactor, size of the shell is significantly varied depending on the apparatus as well. In the multi-tubular reactor having, for example, 5000 or more of the reaction tubes, the inner diameter of the shell is 3 m or more. Therefore, in the multi-tubular reactor having, 10000 or more of the reaction tubes, the inner diameter of the shell is generally 4 m or more. Herein, the outer diameter of the reaction tube which can be located in the shell is generally within a range from 1 to 5 cm, preferably generally from 2 to 3 cm.

However, in case the reaction tube which can be determined according to the method as described above is provided with the thermometer 20 to form the temperature-measuring reaction tube 10m, the condition for the reaction which may be occurred in the reaction tube 10, and the like, can be appropriately understood, and the conditions in the shell 2 can be appropriately controlled, even if the inner diameter of the shell 2 of the multi-tubular reactor 1 according to the present invention is large (or even in 3 m or more).

In the multi-tubular reactor, the number of the reaction tubes which can be located in the shell and size of the shell are significantly varied depending on the apparatus. Therefore, the distance between the reaction tubes may be varied, and the flow resistance in the radial direction when the heat transfer medium flows between the reaction tubes may be varied, even in case of the arrangement in the above-described triangular configuration is employed.

Furthermore, regarding the reaction tube, if the length of the part where the heat transfer medium contacts with the reaction tube is varied, the flow resistance may be varied in a direction toward the central axis of the shell or in the radial outward direction, when the heat transfer medium flows between the reaction tubes. Particularly, in case the number of the reaction tubes is increased, the flow resistance tends to be increased. In this manner, when the flow resistance is increased, a pump with a high performance is required and therefore the cost of the equipment is increased in order to flow the heat transfer medium (HTM) in a given amount.

However, according to the present invention, a ratio (L/D) of a length (L) between the central axis of any one reaction tube and the central axis of at least one reaction tube next to the reaction tube relative to a diameter (D) of said any one reaction tube is set within a range from 1.2 to 1.6. Thereby, the condition of the contact between the heat transfer medium (HTM) and the reaction tube can be improved while the flow resistance of the heat transfer medium (HTM) can be restrained.

EXAMPLES

In the examples of the present invention, flow condition of the heat transfer medium was analyzed by a numerical simulation on the multi-tubular reactor wherein a plurality of the reaction tubes were provided so as to be in the above-described triangular configuration.

In the numerical simulation, flow condition of the heat transfer medium on a cross section of the multi-tubular reactor was analyzed in case of the disk-and-doughnut type baffles 5, particularly ring-form baffles 5a were provided in the cylindrical shell, for example, as shown in FIG. 2, in order to analyze the flow in the radial direction, which flow could be generated in the reactor.

Herein, when the plurality of the reaction tubes were arranged in the triangular configuration, the flow could be formed relative to the central axis of the cylindrical shell of the reactor in symmetry about the axis. Therefore, this numerical simulation was carried out only in ⅙ area (i.e., 60° area) of the entire cross section of the multi-tubular reactor, as it is shown in FIG. 4, but it did not carried out on the entire cross section.

A model of the multi-tubular reactor used in this numerical simulation was as follows.
(Multi-Tubular Reactor)
  Inner diameter φ1 of the shell (diameter): 4970 mm
  Diameter φ2 of flow-in opening for the heat transfer medium (through-hole provided at the center part of the baffle 5a): 750 mm
  Outer diameter of the reaction tube: 27.3 mm
  Arrangement of the reaction tubes: triangular configuration
  Pitch of the reaction tubes (distance between the central axes of two neighboring reaction tubes): 34.6 mm
(Calculation Conditions)
  Calculation was carried out by "FLUENT Ver.6.3.26" which was a general-purpose fluid analysis software provided by ANSYS Japan K.K.
  Calculation conditions were as follows.
  Heat transfer medium: density 1853 kg/m$^3$, viscosity 0.00316 Pa·s
  Turbulence model: RNG K-ε
  Ratio of heat transfer medium flow to reaction tube number (flow/reaction tube number): 0.3 m$^3$/number Furthermore, tube-outside film heat transfer coefficient for the reaction tube was determined in order to observe the effects on the heat transfer by difference between flow conditions.

Calculation was similarly carried out by "FLUENT Ver.6.3.26", which was the general-purpose fluid analysis software provided by ANSYS Japan K.K., according to the above-described calculation.

Figure 7:
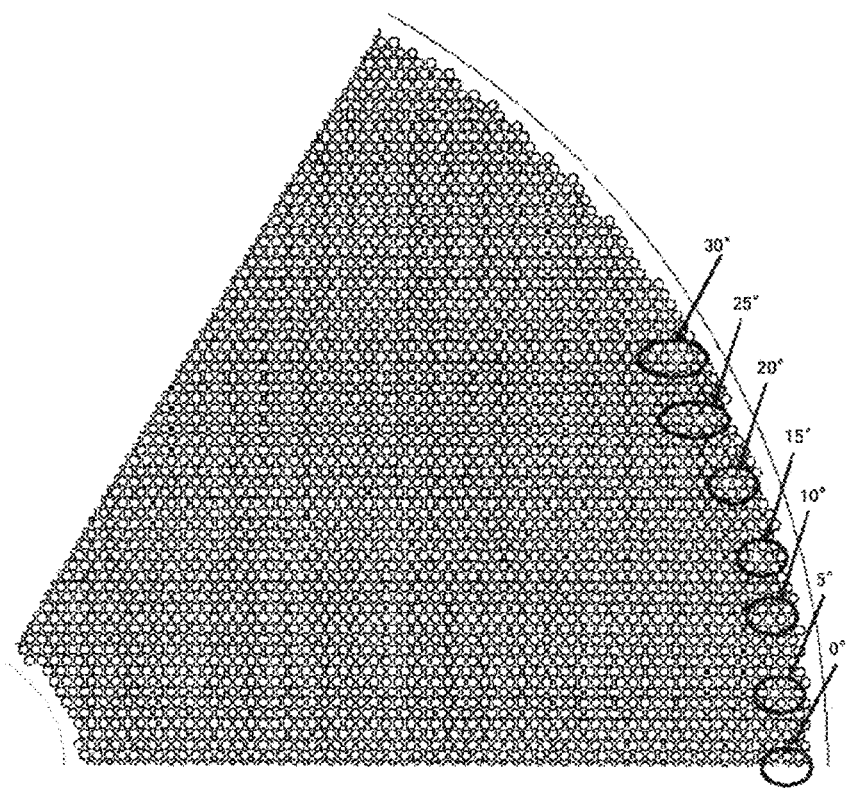
FIGS. 7(A) and 7(B) are figures showing results of numerical simulations in the examples.

Herein, the tube-outside film heat transfer coefficient was determined for the reaction tube in the second row before the most outer row (see FIG. 7(B)). The reason is that the reaction tube in the most outer row has a flow condition of the heat transfer medium, which is significantly different from that of the other reaction tube in the other location.

Figure 5:
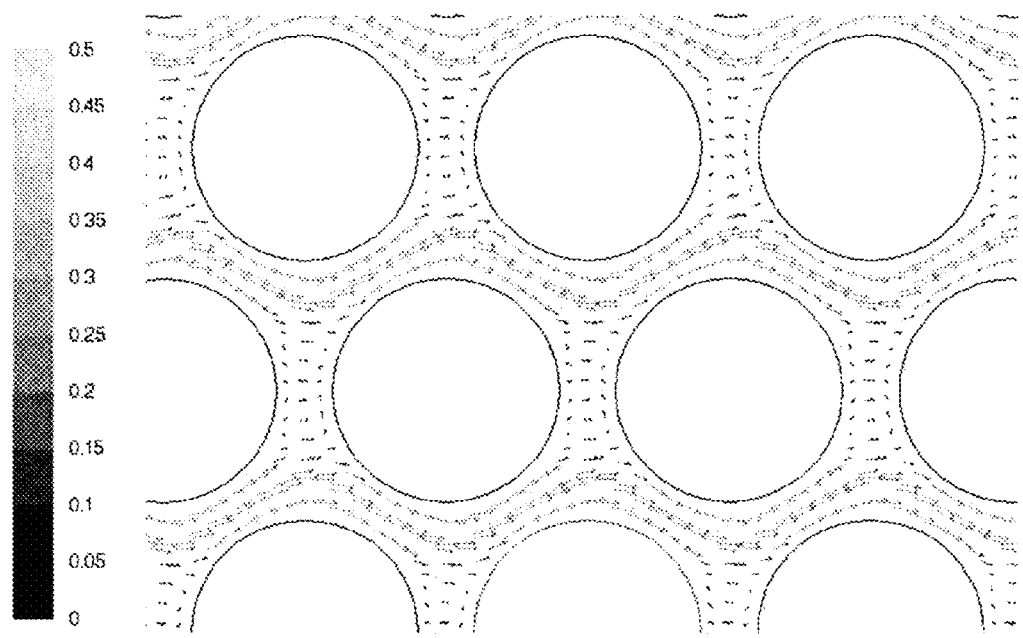
FIGS. 5(A) and 5(B) are figures showing results of numerical simulations in the examples.
Figure 5:
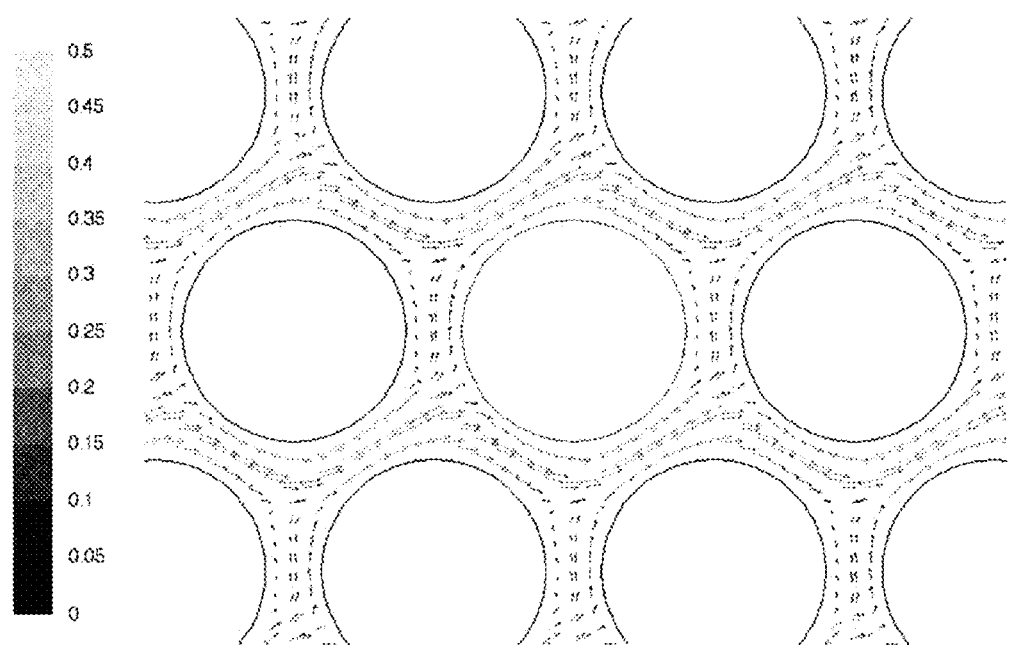
Figure 6:
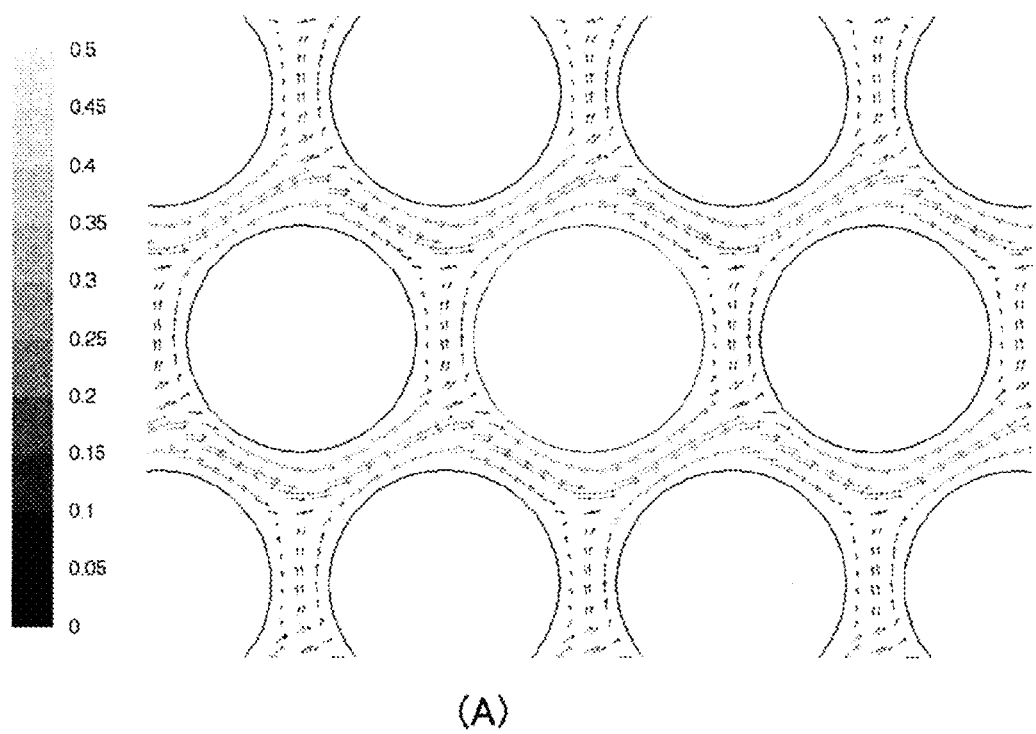
FIGS. 6(A) and 6(B) are figures showing results of numerical simulations in the examples.
Figure 6:
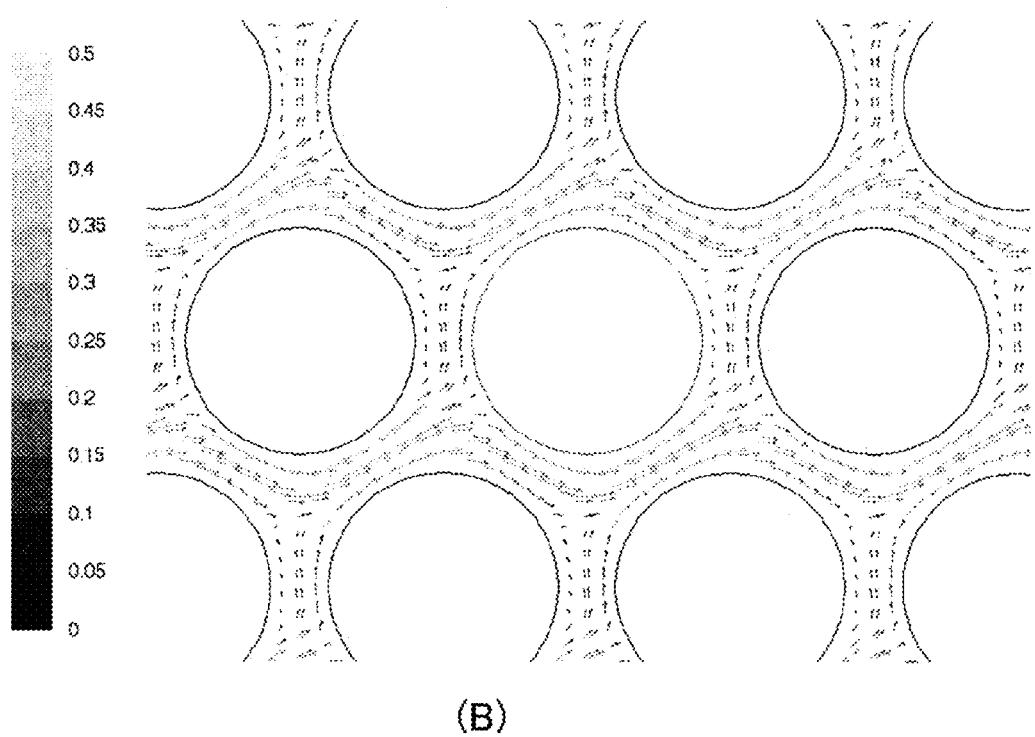

Results of the numerical simulations are shown in FIG. 5 and FIG. 6.

Hereinafter, "temperature-measuring reaction tube having an adjacent reaction tube wherein degree of the angle between the base line BL and the connect line CL is A degree (°)" is simply referred to as "temperature-measuring reaction tube of A degree".

As shown in FIG. 5(A), around the "temperature-measuring reaction tube of 0 degree", formation of one part (or pool) with the flow of the heat transfer medium being very slow can be seen between the reaction tubes.

Whereas, presence of the other part wherein the flow of the heat transfer medium is rectified and the flow rate of the heat transfer medium is increased can be seen between the reaction tubes.

In this manner, around the "temperature-measuring reaction tube of 0 degree", the contrastive flow conditions are formed, which comprise the pooling part and the part where the velocity of the heat transfer medium is high. Therefore, it can be seen that the contacting efficiency between the reaction tube and the heat transfer medium is low.

As shown in FIG. 5(B), around the "temperature-measuring reaction tube of 10 degree", the flow running into the reaction tube is generated, and some of the separated flows of the heat transfer medium are generated after the collision with the reaction tube. However, the pool exists between the reaction tubes. Therefore, it can be seen that the contacting efficiency between the reaction tube and the heat transfer medium is still low.

Whereas, as shown in FIG. 6(A), around the "temperature-measuring reaction tube of 20 degree", the separated flows of the heat transfer medium are formed after the collision with the reaction tube, and the pool is rarely observed between the reaction tubes. Therefore, it can be seen that the contacting efficiency between the reaction tube and the heat transfer medium is significantly improved.

In addition, as shown in FIG. 6(B), around the "temperature-measuring reaction tube of 30 degree", the flow running into the reaction tube is generated, and the flow of the heat transfer medium is equally separated after the collision with the reaction tube to form flows along the reaction tube. Namely, around the "temperature-measuring reaction tube of 30 degree", it can be seen that effective contact between the reaction tube and the heat transfer medium can be established.

In addition, the tube-outside film heat transfer coefficient was determined. As shown in Table of FIG. 7(A), it can be seen that the tube-outside film heat transfer coefficient may be apparently decreased and the improvement rate may be less than 100%, among the "temperature-measuring reaction tube of 0 degree" and the "temperature-measuring reaction tube of 15 degree", particularly at the "temperature-measuring reaction tube of 5 degree" and at the "temperature-measuring reaction tube of 10 degree". Furthermore, it can be seen that the tube-outside film heat transfer coefficient is significantly improved and the improvement rate is apparently increased over 100%, in case of the degree of the contact angle is increased over 15 degree, for example, it is at the "temperature-measuring reaction tube of 20 degree", at the "temperature-measuring reaction tube of 25 degree", and at the "temperature-measuring reaction tube of 30 degree".

Accordingly, the condition in the shell can be appropriately controlled so that the formation of the hot spot or the cold spot is prevented, as shown by the numerical simulation, by utilizing the date of the temperature measured by the thermometer provided in the reaction tube having lowered contacting efficiency among the "temperature-measuring reaction tube of 0 degree" and the "temperature-measuring reaction tube of 15 degree".

As described above, as shown in FIG. 7(A), the tube-outside film heat transfer coefficient is varied depending on the variation of the degree of the angle. It can be seen that the tube-outside film heat transfer coefficient is significantly improved with the measuring location being changed from the temperature-measuring reaction tube of 0 degree to the temperature-measuring reaction tube of 30 degree, particularly in case of the contact angle is more than 15 degree.

Namely, depending on the above-described change in the flow condition of the heat transfer medium, it can be seen that the heat transfer condition between the reaction tube and the heat transfer medium can be improved.

As described above, it can be seen that the flow condition of the heat transfer medium is varied, in the circumferential direction of the shell, in the multi-tubular reactor, wherein the reaction tubes are provided so as to be in the triangular configuration, and that the contacting efficiency between the reaction tube and the heat transfer medium is varied.

Furthermore, from the above-described results of the numerical simulations, it can be seen that the contacting efficiency between the reaction tube and the heat transfer medium can be significantly improved among the "temperature-measuring reaction tube of 10 degree" and the "temperature-measuring reaction tube of 20 degree", wherein the angle of 15 degree is a specific border point (see Table in FIG. 7(A)).

Herein, by improving the contacting efficiency between the reaction tube and the heat transfer medium, it can be seen that the heat transfer condition between the reaction tube and the heat transfer medium can be improved.

Herein, this application claims priority based on Japanese Patent Application No. 2012-085158 filed on Apr. 4, 2012 in Japan. The entire disclosure thereof is incorporated herein by reference.

INDUSTRIAL APPLICABILITY

The multi-tubular reactor according to the present invention is applicable to an apparatus for producing any substance with an exothermic or endothermic reaction.

EXPLANATION OF LETTERS AND NUMERALS

1: multi-tubular reactor
2: shell
5: disk-and-doughnut type baffle(s)
10: reaction tube
10$m$: temperature-measuring reaction tube
20: thermometer
BL: base line (line through central axis of temperature-measuring reaction tube and central axis of shell)
CL: connect line (line through central axis of temperature-measuring reaction tube and central axis of at least one adjacent reaction tube next to the temperature-measuring reaction tube)
HTM: heat transfer medium

The invention claimed is:
1. A multi-tubular reactor comprising a cylindrical shell, a plurality of reaction tubes located in the shell, and a disk-and-doughnut type baffle, characterized in that the reaction tubes are arranged so as to be in a triangular zigzag arrangement having units, each of which has three neighboring reaction tubes as one single unit, wherein the central axes of these three reaction tubes are located at three summits of a virtual equilateral triangle, respectively, one or more of the reaction tubes is/are a temperature-measuring reaction tube(s) provided with a thermometer, and a line through a central axis of the temperature-measuring reaction tube and a central axis of the shell forms an angle from 0 to 15 degree with a line through the central axis of the temperature-measuring reaction tube and a central axis of at least one adjacent reaction tube next to the temperature-measuring reaction tube, in a cross section of the reactor perpendicular to the central axis of the shell.

2. The multi-tubular reactor according to claim 1, characterized in that the reactor is a fixed bed multi-tubular reactor to be used for a gas-solid heterogeneous reaction.

3. The multi-tubular reactor according to claim 2, characterized in that propylene, isobutylene, t-butyl alcohol, or a mixture of two or more thereof is oxidized in a gas phase with a gas containing molecular oxygen to produce (meth) acrolein and/or (meth)acrylic acid.

4. The multi-tubular reactor according to claim 1, characterized in that the shell has an inner diameter of 3 m or more.

5. The multi-tubular reactor according to claim 1, characterized in that the number of the reaction tubes located in the shell is 5000 or more.

6. The multi-tubular reactor according to claim 1, characterized in that a ratio (L/D) of a length (L) between central axes of two reaction tubes next to each other relative to an outer diameter (D) of the reaction tubes is from 1.2 to 1.6.

7. The multi-tubular reactor according to claim 1, characterized in that a heat transfer medium flows in the cylindrical shell and comes into contact with the reaction tubes.

8. The multi-tubular reactor according to claim 7, characterized in that a part where the heat transfer medium contacts with the reaction tube has a length of 1.3 m or more.

9. The multi-tubular reactor according to claim 1, characterized in that the temperature-measuring reaction tube is located in a sector area having a central angle of 30° in a cross section of the reactor perpendicular to the central axis of the cylindrical shell.

10. A production method of a multi-tubular reactor comprising a cylindrical shell, a plurality of reaction tubes located in the shell, and a disk-and-doughnut type baffle, characterized in that the method comprises:

arranging the reaction tubes so as to be in a triangular zigzag arrangement having units, each of which has three neighboring reaction tubes as one single unit, wherein the central axes of these three reaction tubes are located at three summits of a virtual equilateral triangle, respectively, and providing a thermometer to one or more of the reaction tube(s) to form a temperature-measuring reaction tube(s), wherein a line through a central axis of the temperature-measuring reaction tube and a central axis of the shell forms an angle from 0 to 15 degree with a line through the central axis of the temperature-measuring reaction tube and a central axis of at least one adjacent reaction tube next to the temperature-measuring reaction tube, in a cross section of the reactor perpendicular to the central axis of the shell.

11. The production method according to claim 10, characterized in that the multi-tubular reactor is a fixed bed multi-tubular reactor to be used for a gas-solid heterogeneous reaction.

12. The production method according to claim 11, characterized in that propylene, isobutylene, t-butyl alcohol, or a mixture of two or more thereof is oxidized in a gas phase with a gas containing molecular oxygen to produce (meth) acrolein and/or (meth)acrylic acid during the gas-solid heterogeneous reaction.

13. The production method according to claim 10, characterized in that the shell has an inner diameter of 3 m or more.

14. The production method according to claim 10, characterized in that the number of the reaction tubes located in the shell is 5000 or more.

15. The production method according to claim 10, characterized in that the reaction tubes are located in the shell so that a ratio (L/D) of a length (L) between central axes of two reaction tubes next to each other relative to an outer diameter (D) of the reaction tubes is from 1.2 to 1.6.

16. The production method according to claim 10, characterized in that a heat transfer medium flows in the cylindrical shell and comes into contact with the reaction tubes.

17. The production method according to claim 16, characterized in that a part where the heat transfer medium contacts with the reaction tube has a length of 1.3 m or more.

18. The production method according to claim 10, characterized in that the temperature-measuring reaction tube is located in a sector area having a central angle of 30° in a cross section of the reactor perpendicular to the central axis of the cylindrical shell.

19. The multi-tubular reactor according to claim 1, characterized in that a ratio of a diameter of a through-hole of the baffle in a doughnut shape to a diameter of the baffle in a disk shape is from 1:2 to 1:3.

20. The production method according to claim 10, characterized in that a ratio of a diameter of a through-hole of the baffle in a doughnut shape to a diameter of the baffle in a disk shape is from 1:2 to 1:3.

21. A multi-tubular reactor comprising a cylindrical shell, a plurality of reaction tubes located in the shell, and a disk-and-doughnut type baffle, wherein the reaction tubes are arranged so as to be in a triangular zigzag arrangement having units, each of which has three neighboring reaction tubes as one single unit, wherein the central axes of these three reaction tubes are located at three summits of a virtual equilateral triangle, respectively, one or more of the reaction tubes is/are a temperature-measuring reaction tube(s) provided with a thermometer, a heat transfer medium flows in the cylindrical shell and comes into contact with the reaction tubes, a line through a central axis of the temperature-measuring reaction tube and a central axis of the shell forms an angle from 0 to 15 degree with a line through the central axis of the temperature-measuring reaction tube and a central axis of at least one adjacent reaction tube next to the temperature-measuring reaction tube, in a cross section of the reactor perpendicular to the central axis of the shell, condition in the shell is controlled by utilizing temperature data measured by the thermometer provided to the temperature-measuring reaction tube to prevent formation of hot spot or cold spot, and the reactor is a fixed bed multi-tubular reactor to be used for a gas-solid heterogeneous reaction.

22. A production method of a multi-tubular reactor comprising a cylindrical shell, a plurality of reaction tubes located in the shell, and a disk-and-doughnut type baffle, comprising:

arranging the reaction tubes so as to be in a triangular zigzag arrangement having units, each of which has three neighboring reaction tubes as one single unit, wherein the central axes of these three reaction tubes are located at three summits of a virtual equilateral triangle, respectively, providing a thermometer to one or more of the reaction tube(s) to form a temperature-measuring reaction tube(s), wherein a heat transfer medium flows in the cylindrical shell and comes into contact with the reaction tubes, a line through a central axis of the temperature-measuring reaction tube and a central axis of the shell forms an angle from 0 to 15 degree with a line through the central axis of the temperature-measuring reaction tube and a central axis of at least one adjacent reaction tube next to the temperature-measuring reaction tube, in a cross section of the reactor perpendicular to the central axis of the shell, condition in the shell is controlled by utilizing temperature data measured by the thermometer provided to the temperature-measuring reaction tube to prevent formation of hot spot or cold spot, and the reactor is a fixed bed multi-tubular reactor to be used for a gas-solid heterogeneous reaction.

* * * * *